United States Patent
Guzzonato et al.

(10) Patent No.: US 10,656,130 B2
(45) Date of Patent: May 19, 2020

(54) ELEMENTAL ANALYSIS SYSTEM AND METHOD WITH A REACTOR HAVING TWO METAL ZEOLITE NITROGEN OXIDES REDUCTION REACTION ZONES

(71) Applicant: Thermo Fisher Scientific (Bremen) GmbH, Bremen (DE)

(72) Inventors: Antonella Guzzonato, Bremen (DE); Christopher Brodie, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 197 days.

(21) Appl. No.: 15/582,965

(22) Filed: May 1, 2017

(65) Prior Publication Data

US 2017/0336374 A1    Nov. 23, 2017

(30) Foreign Application Priority Data

May 17, 2016 (GB) .................................. 1608643.1
Mar. 16, 2017 (GB) .................................. 1704177.3

(51) Int. Cl.
  *G01N 33/00* (2006.01)
  *G01N 30/62* (2006.01)
  (Continued)

(52) U.S. Cl.
  CPC ......... *G01N 33/0036* (2013.01); *G01N 30/62* (2013.01); *G01N 30/88* (2013.01);
  (Continued)

(58) Field of Classification Search
  CPC ........ G01N 33/00; G01N 30/62; G01N 30/88; H01J 49/00; H01J 49/02
  (Continued)

(56) References Cited

U.S. PATENT DOCUMENTS 4,297,328 A * 10/1981 Ritscher .............. B01D 53/945
                                             423/213.2
4,778,665 A * 10/1988 Krishnamurthy .. B01D 53/8628
                                             208/113

(Continued)

FOREIGN PATENT DOCUMENTS

CN   103091353 A   5/2013
CN   104483168 A   4/2015

(Continued)

OTHER PUBLICATIONS

Merritt, D. A. et al, Journal of the American Society for Mass Spectrometry 1994, 5, 387-397.*

(Continued)

*Primary Examiner* — Arlen Soderquist
(74) *Attorney, Agent, or Firm* — Charles B. Katz

(57) ABSTRACT

An elemental analysis system includes a reactor having at least one reduction reaction zone including a metal zeolite that can reduce nitrogen oxides ($NO_x$) to molecular nitrogen ($N_2$) by selective catalytic reduction. Correspondingly, a method of elemental analysis includes providing a reactor having at least one reduction reaction zone including a metal zeolite and reducing nitrogen oxides ($NO_x$) to molecular nitrogen ($N_2$) by selective catalytic reaction on the metal zeolite.

33 Claims, 12 Drawing Sheets

(51) Int. Cl.
*G01N 30/88* (2006.01)
*H01J 49/00* (2006.01)
*H01J 49/02* (2006.01)
*G01N 30/06* (2006.01)

(52) U.S. Cl.
CPC ...... *G01N 33/0013* (2013.01); *H01J 49/0031* (2013.01); *H01J 49/025* (2013.01); *G01N 2030/067* (2013.01); *G01N 2030/8868* (2013.01)

(58) Field of Classification Search
USPC ........................................................ 436/106
See application file for complete search history.

(56) References Cited

U.S. PATENT DOCUMENTS

| | | | | |
|---|---|---|---|---|
| 4,962,075 A * | 10/1990 | Green | .................. | B01D 53/945 502/64 |
| 5,041,272 A * | 8/1991 | Tamura | .............. | B01D 53/9418 423/212 |
| 5,080,876 A * | 1/1992 | Izumi | ................. | B01D 53/8625 423/239.2 |
| 5,116,586 A * | 5/1992 | Baacke | .............. | B01D 53/9418 423/239.2 |
| 5,143,707 A * | 9/1992 | Beck | ................... | B01D 53/9418 423/239.2 |
| 5,149,512 A * | 9/1992 | Li | ....................... | B01D 53/8625 423/212 |
| 5,343,702 A * | 9/1994 | Miyajima | ................ | F01N 3/20 123/431 |
| 5,433,933 A * | 7/1995 | Eshita | .................. | B01D 53/945 423/213.2 |
| 5,449,504 A * | 9/1995 | Kasahara | ........... | B01D 53/9418 423/213.2 |
| 5,514,355 A * | 5/1996 | Eshita | .................. | B01D 53/945 423/212 |
| 5,612,225 A * | 3/1997 | Baccanti | ................ | G01N 30/12 422/78 |
| 5,643,542 A * | 7/1997 | Leyrer | ................. | B01D 53/945 423/212 |
| 5,891,409 A * | 4/1999 | Hsiao | .................. | B01D 53/323 423/239.1 |
| 6,093,378 A * | 7/2000 | Deeba | .................. | B01D 53/945 423/213.5 |
| 6,368,571 B1 * | 4/2002 | Vempati | .................. | C01B 39/38 423/709 |
| 6,653,143 B2 * | 11/2003 | Ragaglia | ................ | G01N 31/12 422/78 |
| 2001/0018218 A1 * | 8/2001 | Ragaglia | ................ | G01N 31/12 436/160 |
| 2003/0162649 A1 * | 8/2003 | Basso | ...................... | B01J 29/06 502/64 |
| 2005/0101473 A1 * | 5/2005 | Marshall | ........... | B01D 53/8628 502/60 |
| 2005/0207957 A1 * | 9/2005 | Sugiyama | .......... | B01D 53/8628 423/239.2 |
| 2010/0260652 A1 * | 10/2010 | Nakane | .............. | B01D 53/9413 423/213.2 |
| 2011/0210242 A1 * | 9/2011 | Bateman | ................. | H01J 27/02 250/282 |

FOREIGN PATENT DOCUMENTS

| | | | |
|---|---|---|---|
| CN | 104582815 A | | 4/2015 |
| EP | 1707253 B1 | | 8/2008 |
| GB | 2533398 A | | 6/2016 |
| WO | 02/057007 | * | 7/2002 |
| WO | 2014/025530 A1 | | 2/2014 |

OTHER PUBLICATIONS

Meier-Augenstein, A., Journal of Chromatography A 1999, 842, 351-371.*
De Lucas, A. et al, Journal of Molecular Catalysis A: Chemical 2005, 225, 47-58.*
Thermo Scientific FLASH 2000 HT Elemental Analyzer for Isotope Ratio MS 2010, 8 pages, downloaded from https://fscimage.fishersci.com/images/D13085~.pdf.*
Valero-Romero, M. J. et al, Catalysis Science & Technology 2016, 14 pages.*
Calderone et al., "Characterization of European Wine Glycerol: Stable Carbon Isotope Approach," J. Agric. Food Chem., 52, 5902-5906, 2004.
Fedeeva et al., "Elemental Analysis of Organic Compounds with the Use of Automated CHNS Analyzers," J. of Anal. Chem., 63(11), 1094-1106, 2008.
Kracht, "Comparison of Isotope Analysis with Single Reactor Combustion and Conventional Combustion in a Dual Reactor Setup," Application Note 30190, 2 pgs., 2010.

* cited by examiner

ELEMENTAL ANALYSIS SYSTEM AND METHOD WITH A REACTOR HAVING TWO METAL ZEOLITE NITROGEN OXIDES REDUCTION REACTION ZONES

CROSS-REFERENCE TO RELATED APPLICATIONS

This application claims the priority benefit under 35 U.S.C. § 119 to British Patent Application No. 1608643.1, filed on May 17, 2016 and British Patent Application No. 1704177.3, filed on Mar. 16, 2017, the disclosures of which are incorporated herein by reference.

FIELD OF THE INVENTION

The present invention is generally directed to an elemental analysis system and method. More specifically, the present invention is directed an elemental analysis system and method that includes a reactor having at least one reduction reaction zone including a metal zeolite that can reduce nitrogen oxides ($NO_x$) to molecular nitrogen ($N_2$) by selective catalytic reduction.

BACKGROUND

Elemental analysis (EA) involving combustion/reduction and/or pyrolysis is a widely used technique for the quantification of elemental concentrations of hydrogen, carbon, nitrogen, oxygen, and sulphur in organic and inorganic materials. Interfaced with isotope ratio mass spectrometry (IRMS), EA is commonly employed as a technique for the measurement of stable isotope ratios of the aforementioned elements. See Calderone et al, (2004) J. Agric. Food Chem., 52, 5902-5906, and Fadeeva et al, (2008) J. Anal. Chem. 63(11), 1094-1106, the disclosures of both references being hereby incorporated by reference in their entirety (however, where anything in the incorporated references contradicts anything stated in the present application, the present application prevails). The general way of reporting stable isotope ratios from EA-IRMS analysis is using "delta notation" (δ-notation). IRMS allows precise measurement of isotope abundance in a sample gas, which allows determination of a ratio of the heavy to light isotope (R), such as:

$$R = \frac{\text{Heavy Isotope}}{\text{Light Isotope}} = \frac{^{13}C}{^{12}C} = \frac{^{15}N}{^{14}N} = \frac{^{18}O}{^{16}O}$$

The δ-notation is the stable isotope ratio of an unknown sample relative to a standard (i.e. reference material) of known isotope value, calculated as:

$$\delta[\%] = \frac{R_{(Sample)} - R_{(Standard)}}{R_{(Standard)}} * 1000 = \left(\frac{R_{(Sample)}}{R_{(Standard)}} - 1\right) * 1000$$

For EA-IRMS, two approaches are typically used. One approach uses two reactors (hereafter Approach 1), where the combustion and reduction processes occur in separate reactors heated by different furnaces or alternatively by the same furnace. Another approach combines the combustion and reduction processes into the same reactor (hereafter Approach 2), which is heated by the same furnace.

The analysis of hydrogen, carbon, nitrogen and sulphur is achieved by combusting a sample matrix in a reactor held at a temperature in a range of between 400° C. and 1,100° C., but ideally in a range of between 950° C. and 1,100° C. Generally, samples are sealed in tin capsules (alternatively, silver or aluminum capsules) and introduced to the combustion reactor by an autosampler in a flow of carrier gas, such as helium (for EA-IRMS), or argon or nitrogen (EA analysis only). The carrier gas flow maintains pressure and temperature regimes in the reactor, minimizes introduction of contaminant gases, such as air, and reduces damage to any materials or chemicals inside the system. Elemental analyzers require carrier flows of up to 1,000 ml/min depending on the volume to be flushed, the largest volume generally being the reactor. The typical operating flow rate through the reactor, however, is in the range of between 0.2 ml/min and 300 ml/min, such as in the range of between 40 ml/min and 300 ml/min, or between 40 ml/min and 200 ml/min (EA analysis only), depending on the reactor size, and a purge flow to the autosampler is generally in a range of between 20 ml/min and 300 ml/min. At or near the point of sample introduction, an injection of oxygen gas ($O_2$) may or may not occur, depending on the sample matrix, to support the combustion process (Lott et al, Rapid Commun. Mass Spectrom. 2015, 29, 1-8), hereby incorporated by reference in its entirety (however, where anything in the incorporated reference contradicts anything stated in the present application, the present application prevails). At this point, the sample matrix breaks down, and is conveyed by the carrier gas across an oxygen donor compound (e.g., $Cr_2O_3$, $WO_3$), which is designed to ensure complete oxidation of the carbon, nitrogen and sulphur elements evolved from the sample matrix to gaseous oxidized products (e.g., $CO_2$, $NO_x$, $SO_2$). After the oxidation process, the next step in the reaction varies depending on the set-up of the system. In Approach 1 (two reactor system), the gases are then optionally swept across a sulphur/halogen trap and transferred to a reduction reactor, typically via a stainless steel/sulfinert capillary or heated bridge, which contains metallic copper. The reduction reactor is generally held at a temperature in a range of between 450° C. and 900° C., and is designed to reduce $NO_x$ (x=1, 2, 3) gas species to $N_2$, reduce $SO_3$ to $SO_2$ and absorb excess $O_2$ not used in the combustion reaction. After the gases are carried out of the reduction reactor, they are swept through a water trap (e.g., magnesium perchlorate) and/or optionally a $CO_2$/acid gas trap (e.g., carbosorb) before being analyzed. After leaving the reduction reactor, the gases are typically separated on a gas chromatography column or by an adsorption/thermodesorption technique prior to analysis by a thermal conductivity detector (TCD), a flame ionization detector (FID), or an isotope ratio mass spectrometer. In Approach 2, however, after the analyte gas passes across the oxygen donor compound, the oxidized gaseous products are conveyed onto metallic Cu within the same reactor, where the same chemical reaction as in Approach 1 occurs: a sulphur/halogen trap may also be present in the lower section of the reactor (e.g., $AgCoO_4$ or silver wool). Thereafter, the gas is conveyed from the reactor through a water trap and/or optionally a $CO_2$/acid gas trap before gas separation and detection as in Approach 1.

A stoichiometric combustion and reduction reaction pathway is necessary for the accurate and precise determination of percent elemental and isotopic measurements of carbon, nitrogen and sulphur. For nitrogen analysis, specifically, the process is designed to produce $N_2$ gas for detection by the TCD and/or isotope ratio mass spectrometer. During the sample combustion process, nitrogen compounds are broken down and subsequently form nitrogen oxides ($NO_x$). These oxides of nitrogen must be stoichiometrically reduced to $N_2$, which is one of the functions of the metallic Cu in the reactor(s) described in Approach 1 and Approach 2.

There is, nevertheless, a need for further improvements in the stoichiometric reduction of $NO_x$ species to $N_2$ before the analyte gas is conveyed from the reactor for separation and subsequent analysis by TCD and/or IRMS.

SUMMARY

In one embodiment, an elemental analysis system includes a reactor having at least one reduction reaction zone including a metal zeolite that can reduce nitrogen oxides ($NO_x$) to molecular nitrogen ($N_2$) by selective catalytic reaction. Correspondingly, a method of elemental analysis includes providing a reactor having at least one reduction reaction zone including a metal zeolite and reducing nitrogen oxides ($NO_x$) to molecular nitrogen ($N_2$) by selective catalytic reaction on the metal zeolite. The metal zeolite can be a ZSM-5 type material. The metal zeolite, typically ZSM-5 type, can have one or more of the following beneficial characteristics: a MFI framework type, a BET surface area of at least 300 $m^2/g$, and/or a weight loss on ignition of less than 12 wt %. In some embodiments, the metal zeolite can include a +2 oxidation state metal, such as at least one of copper, platinum, nickel, and cobalt. The metal content of the metal zeolite can be in a range of between 2.1 wt % and 5.0 wt %. In some embodiments, the metal zeolite can have a grain size in a range of between 0.3 mm and 2.9 mm, such as in a range of between 1 mm and 2 mm, or, in a specific embodiment, the grain size of the metal zeolite can be 1.6 mm. In certain embodiments, the metal zeolite can include carbon in an amount that is at least 70 ppm and less than 200 ppm. An advantage of the system and method described herein is that the metal zeolite can be regenerated "online" in the reactor (e.g., by urea regeneration), thereby extending reactor lifetime and reducing maintenance intervals and system downtime.

In a specific embodiment, the at least one reduction reaction zone can be one zone packed in a single packing unit having a length that is in a range of between 1% and 30% of a length of the reactor. In some embodiments, the at least one reduction reaction zone can be at least two reduction reaction zones of substantially the same length, the lengths being in total in a range of between 1% and 30% of a length of the reactor, i.e., of the total length of the reactor. In certain other embodiments, the at least one reduction reaction zone can be at least two reduction reaction zones of different lengths, such as successively increasing lengths in a direction of gas flow through the reactor, the lengths being in total in a range of between 1% and 30% of a length of the reactor. In embodiments including at least two reduction reaction zones, the zones can be separated from each other by a porous material, the separation having a length in a range of between 1% and 3% of a length of the reactor. In some embodiments, the porous material can include quartz or glass wool.

In another specific embodiment, the at least two reduction reaction zones can be two reduction reaction zones, each reduction reaction zone having a length in a range of between 1% and 15% of a length of the reactor. In yet another specific embodiment, the at least two reduction reaction zones can be three reduction reaction zones, such as three reduction reaction zones of successively increasing lengths in a direction of gas flow through the reactor.

In some embodiments, the reactor can further include an oxidation reaction zone, the oxidation reaction zone being located before, i.e., upstream of, the reduction reaction zone in a direction of gas flow through the reactor. Correspondingly, the method of elemental analysis can include providing an oxidation reaction zone located before, i.e., upstream of, the reduction reaction zone in a direction of gas flow through the reactor, for oxidizing a sample. The sample oxidation in the oxidation reaction zone can include generating combustion product gases including $NO_x$. The combustion product gases can include at least one of $CO_2$ and $SO_2/SO_3$. In these specific embodiments, the reactor can further include an oxygen gas inlet upstream of or into the oxidation reaction zone. In certain embodiments, the oxidation reaction zone can include an oxygen-donor material, such as at least one of chromium trioxide ($Cr_2O_3$), tungsten trioxide ($WO_3$), copper oxide, and a mixture of copper oxide and platinum-coated aluminum oxide.

In certain embodiments, the elemental analysis system further includes a furnace to heat the reactor, wherein the reduction reaction zone and oxidation reaction zone are each configured to be heated to a temperature in the range of between 150° C. and 1,200° C., such as a temperature in the range of between 750° C. and 1,200° C., or a temperature in the range of between 950° C. and 1,100° C. In some embodiments, the reduction reaction zone can be configured to be heated to a different temperature from the oxidation reaction zone, such as a lower temperature than the oxidation reaction zone.

In some embodiments, the elemental analysis system can include an oxygen capture zone, downstream of the reduction reaction zone in a direction of gas flow through the reactor, which can include metallic copper, metallic platinum, metallic nickel, or metallic cobalt, or any combination thereof. The oxygen capture zone can act to remove gaseous oxygen from the gases passing out of the reduction reaction zone.

In certain embodiments, the elemental analysis system can further include a second reactor in fluid communication with the first reactor that contains the reduction reaction zone, the second reactor being located upstream of the first reactor in a direction of gas flow through the first reactor, the second reactor including an oxidation reaction zone. In these specific embodiments, the elemental analysis system can further include a furnace to heat the first reactor to a temperature in the range of between 150° C. and 1200° C., such as a temperature in the range of between 150° C. and 1100° C., or a temperature in the range of between 450° C. and 900° C., and a second furnace to heat the second reactor to a temperature in the range of between 150° C. and 1,200° C. In some embodiments, the temperature of the second reactor can be in the range of between 750° C. and 1,200° C., such as in the range of between 950° C. and 1,100° C. For convenience and lower cost, in some embodiments, the first and second reactors can be located in, i.e., heated by, a single, common furnace. The second reactor can further include an oxygen gas inlet upstream of or into the oxidation reaction zone. In certain embodiments, the oxidation reaction zone can include an oxygen-donor material, such as at least one of chromium trioxide ($Cr_2O_3$), tungsten trioxide ($WO_3$), copper oxide, and a mixture of copper oxide and platinum-coated aluminum oxide.

In some embodiments, the reactor containing the reduction reaction zone can be interfaced to a gas chromatography column located downstream of the reactor in a direction of gas flow. Alternatively, the reactor can be interfaced with a mass spectrometer located downstream of the reactor in a direction of gas flow through the reactor, optionally an isotope ratio mass spectrometer. The gas chromatography column can be interfaced to a thermal conductivity detector (TCD), a flame ionization detector (FID), an infrared (IR) detector, or a mass spectrometer, such as an isotope ratio mass spectrometer. The mass spectrometer can be located downstream of the gas chromatography column in a direction of gas flow, optionally an isotope ratio mass spectrometer including a magnetic sector mass analyzer. The isotope ratio mass spectrometer can have a multicollector detection system for simultaneously detecting two or more spatially separated ion beams, which consist of ions differing in their mass due to the isotopic differences in the gas molecules of the ions. Measurements of these ion beams in multicollector systems allow isotope ratios to be determined.

In embodiments including the second reactor, the first reactor can be interfaced to a gas chromatography column or a mass spectrometer, as described in the preceding paragraph.

In certain embodiments, the elemental analysis system can include a sample introduction system, such as an autosampler located upstream from the reactor for introducing liquid or solid samples into the system. In embodiments including the second reactor, the elemental analysis system can include a sample introduction system, such as an autosampler located upstream from the second reactor for introducing liquid or solid samples into the system.

In another embodiment, a method of elemental analysis of a sample includes introducing into an oxidation reaction zone a sample to be analyzed, optionally using a liquid or solid autosampler, oxidizing the sample in the oxidation reaction zone to generate oxidized products including nitrogen oxides ($NO_x$) from nitrogen present in the sample, reducing the nitrogen oxides to elemental nitrogen in a reactor including at least one reduction reaction zone including a metal zeolite that can reduce nitrogen oxides ($NO_x$) to molecular nitrogen ($N_2$) by selective catalytic reaction, and analyzing the elemental nitrogen using mass spectrometry. In some embodiments, the analyzing can include analyzing the molecular nitrogen ($N_2$) using isotope ratio mass spectrometry (IRMS) and determining therefrom a $\delta^{15}N$ value for the nitrogen produced from the sample material. The analyzing can include analyzing the molecular nitrogen ($N_2$) using isotope ratio mass spectrometry (IRMS) and determining therefrom isotope abundances or an isotope ratio such as $^{14}$N/[14]N (mass 28), $^{15}$N/[14]N (mass 29), and/or $^{15}$N/[15]N (mass 30), as raw isotope ratios and subsequently converting them to $\delta^{15}N$ values for the nitrogen produced from the sample material, or determining % N of the sample. The mass 30 peak can elute substantially simultaneously with the mass 28 and mass 29 peaks in the IRMS analysis. This is indicative that the mass 30 peak is due to [15]$N_2$ and not [14]N[16]O and therefore that substantially complete $NO_x$ to $N_2$ reduction has taken place. The method can further include introducing oxygen upstream of and into the oxidation reaction zone.

The invention has many advantages, including enabling improved accuracy and precision of measured $\delta^{15}N$ values, obtaining a mass 30 ion trace that is proportional to the mass 28 and mass 29 ion traces, in line with expected nitrogen isotope proportions at natural abundance levels, which elutes simultaneously and remains stable throughout the lifetime of the reactor, and is linearly related to the mass 28 and mass 29 ion traces. Additionally, it has significant potential for applications analyzing samples enriched in $^{15}$N relative to natural abundance levels, such as tracer studies. The invention can enable more efficient production of $N_2$ gas from a sample for detection by a TCD, and/or isotope ratio mass spectrometer, giving more accurate nitrogen analysis as a result of the oxides of nitrogen ($NO_x$) being more stoichiometrically reduced to $N_2$ before the analyte gas is conveyed from the reactor for separation and subsequent analysis by the TCD and/or IRMS.

In addition to nitrogen measurements, the reactor of the present invention can be used in EA systems to analyze other elements, such as % C and/or $\delta^{13}C$, and % S and/or $\delta^{34}S$. Mass spectrometry, such as IRMS, can be used to analyze the combustion products such as $CO_2$ or $SO_2$ formed in the system. In some embodiments, a method of elemental analysis of a sample includes introducing into an oxidation reaction zone a sample to be analyzed, oxidizing the sample in the oxidation reaction zone to generate oxidized products from elements present in the sample, reducing one or more oxidized products in a reactor including at least one reduction reaction zone including a metal zeolite, and analyzing an elemental and/or isotopic composition from one or more of the oxidized products using gas chromatography and/or mass spectrometry. In some embodiments, the elements can be carbon, sulphur, and/or nitrogen. The analyzing can include analyzing the oxidized products using isotope ratio mass spectrometry (IRMS) and determining therefrom an isotope ratio. Further details of the IRMS are given elsewhere herein.

BRIEF DESCRIPTION OF THE DRAWINGS

Like reference numerals refer to corresponding parts throughout the several views of the drawings.

DETAILED DESCRIPTION OF EMBODIMENTS

Figure 1:
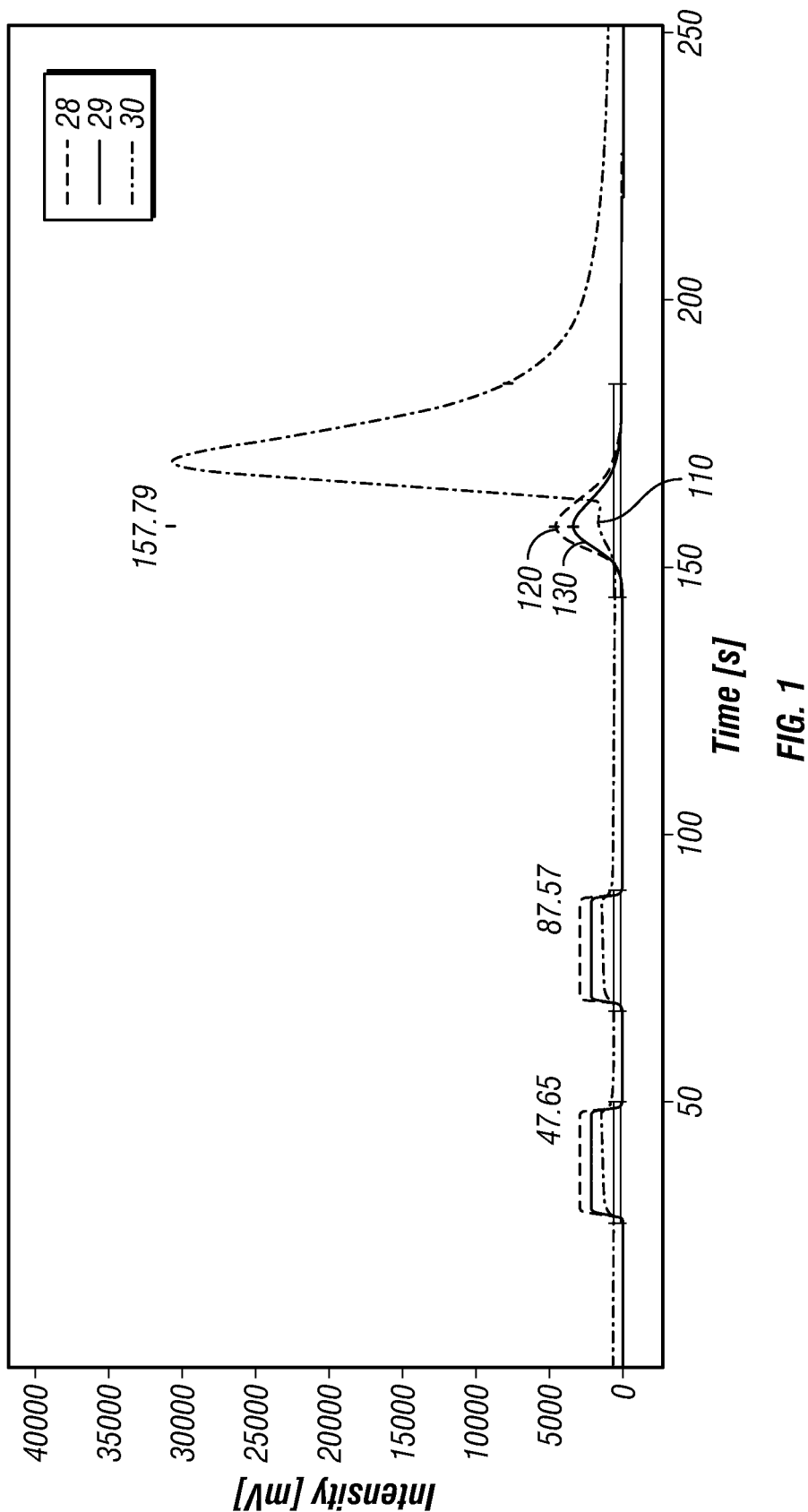
FIG. 1 is a chromatogram illustrating the mass 28, 29, and 30 ion trace behavior in elemental analysis using a reactor of a type known in the art for 40 years.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Any of the features disclosed in this specification may be combined with each other in any combination, except combinations where at least some of such features and/or steps are mutually exclusive. Likewise, features described in non-essential combinations may be used separately (not in combination). Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

As described above, the accurate and precise measurement of elemental nitrogen and stable isotopes of nitrogen in organic and inorganic sample materials relies on the stoichiometric conversion of nitrogen bearing compounds within organic and/or inorganic sample materials to $N_2$ in the reactor. However, the reduction reaction currently used for the conversion of $NO_x$ to $N_2$, using metallic Cu, can be non-stoichiometric in the time desired for analyte gas conveyance through the reactor and data acquisition times, resulting in inaccurate and imprecise $\delta^{15}N$ values. Analyses of $N_2$ gas by EA-IRMS rely on the measurement of $^{14}$N/[14]N (mass 28) and $^{15}$N/[14]N (mass 29).

One reason why mass 30 is not typically used in calculations is that, using the reactors available on the market today, the mass 30 ion trace 110 will gradually rise over the course of the first 1-10 samples, as illustrated in FIG. 1, and remain high throughout the remainder of the analysis. It is also common for the mass 30 ion trace 110 to come close to or exceed the dynamic range of the isotope ratio mass spectrometer, as shown in FIG. 1, meaning that the signal is greater than the dynamic range of the isotope ratio mass spectrometer. It can be clearly seen in FIG. 1 that the intensity of the mass 30 ion trace 110 is much higher than the mass 28 ion trace 120 and the mass 29 ion trace 130, the mass 28 (120) and mass 29 (130) traces resulting only from $N_2$ species. Moreover, over repeated measurements, as illustrated in FIG. 1 by the ion traces after about 150 seconds (s), the intensity of the mass 30 ion trace 110 is not linearly related to the mass 28 (120) and mass 29 (130) ion traces, respectively, as expected at natural abundance levels for nitrogen isotopes, and the chromatographic peak center of the mass 30 ion trace 110 is delayed with respect to the mass 28 (120) and mass 29 (130) ion traces.

As shown in FIG. 1, on EA-IRMS systems, incomplete reduction reaction of [14]N[16]O (m/z 30) to [14]N2 (m/z 28) in the reactor containing metallic Cu is evident from the mass 30 ion trace 110. The mass 30 ion trace 110 (which ideally would be due to [15]$N_2$ molecules) behavior shows a high peak amplitude (between 500 mV to >50,000 mV) that is too high to be caused by [15]$N_2$ (hence it must be due to the interference on m/z 30 coming from [14]N[16]O) and not correlated with the natural or expected ratio with mass 28 and mass 29 based on the natural abundance ratio of nitrogen isotopes. Further, as both NO and $N_2$ are contributing to the m/z 30 trace, the mass 30 ion trace 110 is chromatographically offset from the mass 28 and 29 ion traces 120 and 130 (i.e., mass 30 appears after the mass 28 and mass 29 ion traces). The NO gas is comprised of [14]N[16]O, meaning that $^{14}$N normally measured within the mass 28 and mass 29 ion traces, which are used in the calculations for % N and/or $\delta^{15}N$, is not taken into account. From an isotopic perspective, if NO leaves the reactor because of an incomplete reduction to $N_2$, then the measured $\delta^{15}N$ values will be inaccurate and imprecise. This is problematic for all sample types and all elemental analyzers, presenting a problem for natural abundance and isotopically enriched sample analysis and also a greater challenge for measuring small nitrogen quantities. From the perspective of determining the percent elemental concentration, the data evaluation from the TCD trace will not account for NO during data integration for $N_2$.

The reactors described herein are adapted to enable a stoichiometric reduction of $NO_x$ gas species to $N_2$ before the analyte gas is conveyed from the reactor for separation and subsequent analysis by TCD and/or MS (such as IRMS). The reactors can provide the following characteristics of elemental analysis:

1. a mass 30 ion trace that is proportional to the mass 28 and mass 29 ion traces and which elutes simultaneously with those traces and remains stable substantially throughout the working lifetime of the reactor;

2. a mass 30 ion trace that is linearly related to the mass 28 and mass 29 ion traces, i.e., over repeated measurements on a sample and during the lifetime of the reactor where the sample matrix changes and can be organic, inorganic, or a combination, in nature;

3. accurate and precise $\delta^{13}C$, $\delta^{15}N$ and $\delta^{34}S$ values, when measured individually or together, on organic and inorganic sample matrices regardless of the oxidation state of carbon, nitrogen or sulphur within the sample matrix;

4. measurement of large and small carbon, nitrogen and sulphur amounts (e.g., from 1 ug to >1,000 ug of absolute elemental concentration);

5. online regeneration of the zeolite material, reducing system down-time and maintenance intervals; and 6. increased sample throughput in the reactor, exceeding the sample numbers previously known in the art.

Described herein are reactors for combustion and/or reduction processes by continuous flow (more specifically, plug flow) elemental analysis interfaced with IRMS and/or quantitative elemental concentration analysis by standalone elemental analysis. The reactors described herein typically have a length in a range inclusive of between 20 mm and 470 mm, and an internal diameter in a range of between 0.1 mm and 46 mm, and they can be used in any gas elemental analysis system that employs chromatography and/or adsorption/thermodesorption techniques to separate gas mixtures. Further, the elemental analysis systems described herein are suitable for other systems that rely on reactors for combustion and/or reduction processes, such as gas chromatography and gas chromatography interfaced with mass spectrometry (such as IRMS, but potentially other MS such as quadrupole MS, ion trap MS, time-of-flight MS, Fourier transform MS, and the like).

A variety of reactor configurations are suitable for the reactors for combustion and/or reduction processes described herein. In one aspect, shown in FIGS. 2A, 2B, 2C, and 2D, an elemental analysis system 200 includes a reactor 210 having at least one reduction reaction zone 220 (3 reduction reaction zones 220-1, 220-2, and 220-3 shown in FIG. 2B) including a metal zeolite that can reduce nitrogen oxides ($NO_x$) to molecular nitrogen ($N_2$) by selective catalytic reaction. Although the reactor 210 is shown in a vertical orientation, the reactor 210 can be in a horizontal orientation, or oriented at any angle in-between vertical and horizontal. In one exemplary embodiment, the reactor 210 has a length of 470 mm. The metal zeolite is a ZSM-5 type material that has a MFI framework type, a BET surface area of at least 300 m$^2$/g, and a weight loss on ignition (1000° C.) of less than 12 wt %. In some embodiments, the metal zeolite includes a +2 oxidation state metal, such as at least one of copper, platinum, nickel, and cobalt. The metal content of the metal zeolite is in a range of between 2.1 wt % and 5.0 wt %. A suitable metal zeolite has a copper content of 2.8 wt %, and a BET surface area of 358 m$^2$/g. CuCZP 30E available from Clariant (Bruchmal, Germany). In some embodiments, the metal zeolite can have a grain size in a range of between 0.3 mm and 2.9 mm, such as in a range of between 1 mm and 2 mm, or, in a specific embodiment, the grain size of the metal zeolite can be 1.6 mm. In certain embodiments, the metal zeolite includes carbon in an amount that is at least 70 ppm and less than 200 ppm, such as 100 ppm. The carbon content is believed to improve the thermal stability of the metal zeolite, enabling higher temperature operation of the reactor 210.

Figure 2A:
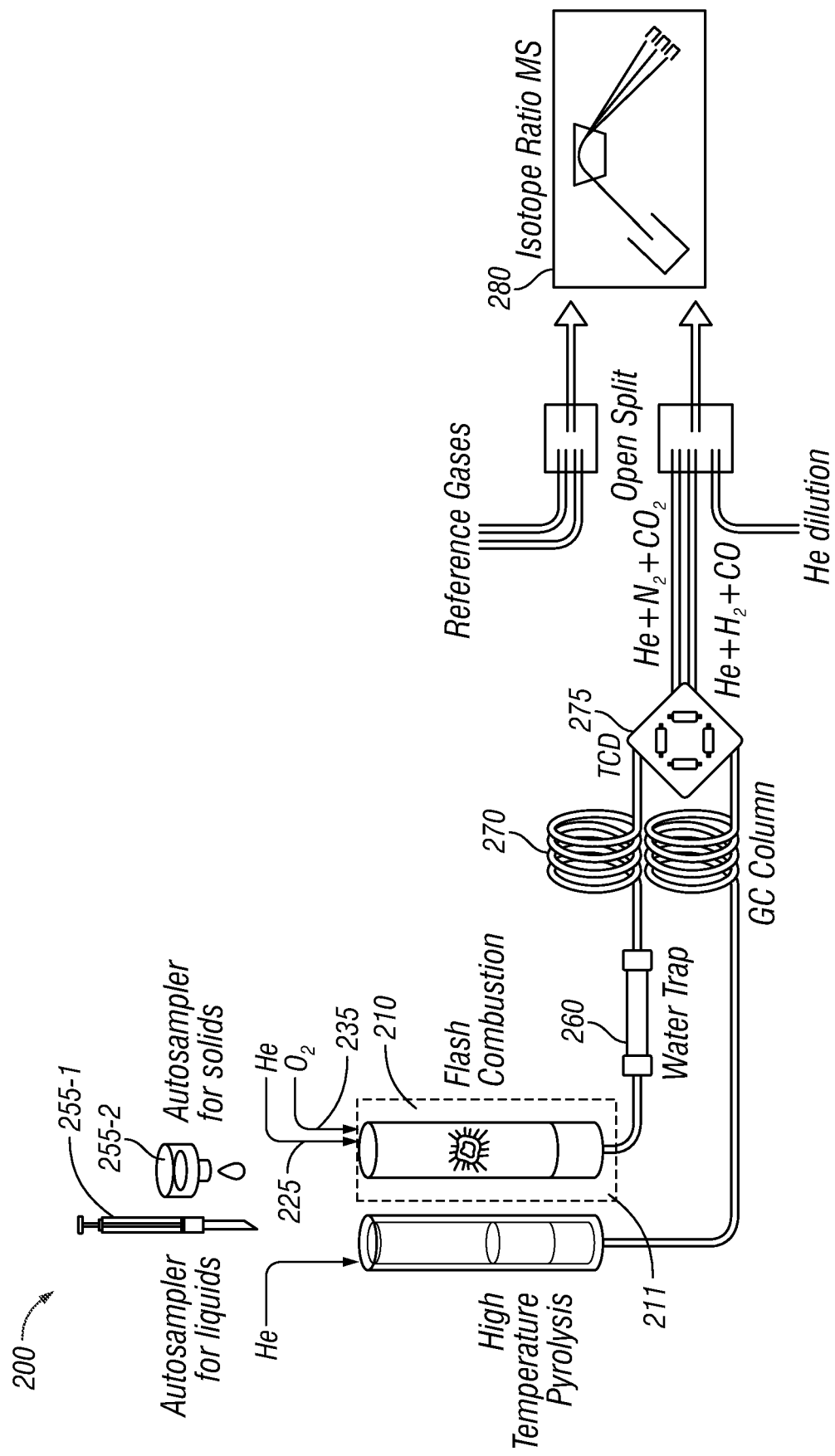
FIG. 2A is a schematic illustration of a single reactor elemental analysis system according to an exemplary embodiment of the invention.

A variety of configurations of the at least one reduction reaction zone 220 are suitable for the reactor 210. In one aspect, as shown in FIG. 2C, the at least one reduction reaction zone is one zone packed in a single packing unit having a length that is in a range of between 0.1% and 50% of a length of the reactor, such as in a range of between 1% and 30%. In one exemplary embodiment, the reduction reaction zone 220 has a length of 100 mm, packed in a reactor 210 having a length of 470 mm.

Figure 2B:
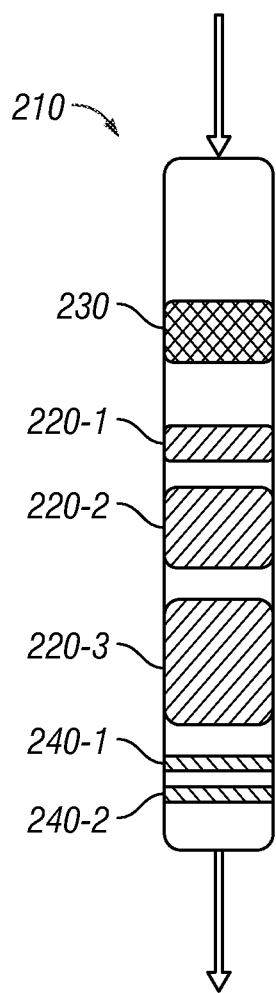
FIG. 2B is a schematic illustration of a reactor including three reduction reaction zones according to an exemplary embodiment of the invention.
Figure 2C:
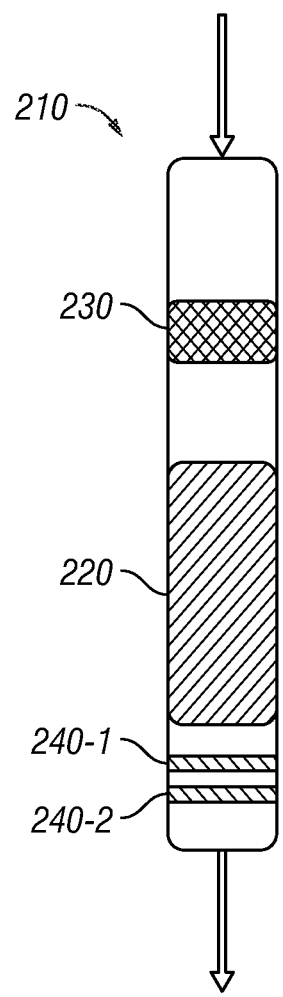
FIG. 2C is a schematic illustration of a reactor including one reduction reaction zone according to an exemplary embodiment of the invention.
Figure 2D:
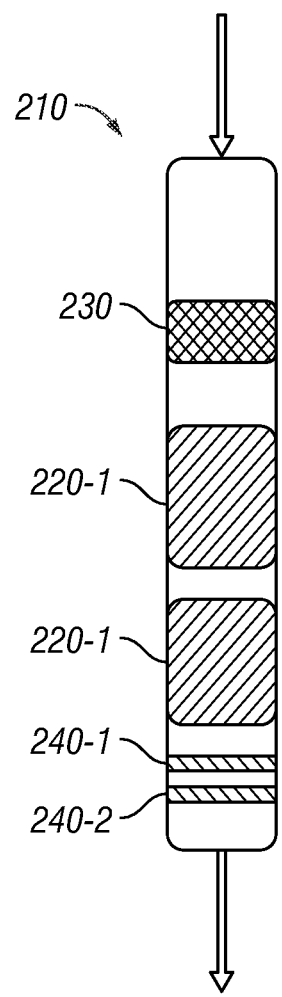
FIG. 2D is a schematic illustration of a reactor including two reduction reaction zones according to an exemplary embodiment of the invention.

As shown in FIGS. 2B, 2C, and 2D, the reactor 210 includes an oxidation reaction zone 230, the oxidation reaction zone 230 being located before the reduction reaction zone 220 in a direction of gas flow through the reactor 210 indicated by inlet and outlet arrows. As shown in FIG. 2A, the reactor 210 optionally includes an oxygen gas inlet 235 upstream of or into the oxidation reaction zone 230. In one exemplary embodiment, 2 ml/sample of $O_2$ were injected through the oxygen gas inlet 235. In addition, the reactor 210 includes a carrier gas inlet 225 upstream of the oxidation reaction zone 230, for injecting carrier gas, such as helium, into the reactor 210.

Turning back to FIGS. 2B, 2C, and 2D, the oxidation reaction zone 230 includes an oxygen-donor material, such as at least one of chromium trioxide ($Cr_2O_3$), tungsten trioxide ($WO_3$), copper oxide, and a mixture of copper oxide and platinum-coated aluminum oxide. The length of the oxidation reaction zone 230 is in a range of between 1% and 30% of the length of the reactor 210, preferable in a range of between 4% and 15% of the length of the reactor 210. In one exemplary embodiment, the oxidation reaction zone 230 has a length of 50 mm.

As shown in FIGS. 2B, 2C, and 2D, the reactor 210 also optionally includes at least one oxygen capture zone 240 (two oxygen capture zones 240-1 and 240-2 shown in FIGS. 2B, 2C, and 2D), downstream of the reduction reaction zone, that can include metallic copper, metallic platinum, metallic nickel, or metallic cobalt, or any combination thereof. The total length of the oxygen capture zone is in a range of between 1% and 15%, preferably in a range of between 1% and 8%, of the length of the reactor 210. In one aspect, the oxygen capture zones 240-1 and 240-2 comprise metallic copper, in two zones each having a length of 20 mm, or two zones of successively increasing length in a direction of gas flow through the reactor, e.g., 20 mm preceded by 10 mm separated by a porous material, such as quartz or glass wool.

As shown in FIG. 2D, the at least one reduction reaction zone can be two reduction reaction zones 220-1 and 220-2 of substantially the same length, the lengths being in total in a range of between 1% and 30% of the length of the reactor 210, each reduction reaction zone having a length in a range of between 1% and 15% of the length of the reactor 210. Alternatively, the two reduction reaction zones 220-1 and 220-2 can have successively increasing lengths in a direction of gas flow through the reactor, the lengths being in total in a range of between 1% and 30% of the length of the reactor 210. Preferably, the second reduction reaction zone 220-2 is at least 1.1 times longer, or at least 1.2 times longer, or at least 1.5 times longer, or at least 2 times longer, or at least 2.5 times longer, or at least 3 times longer, or at least 4 times longer than the first reduction reaction zone 220-1. Preferably, the second reduction reaction zone 220-2 is up to 6 times longer, or up to 5 times longer, or up to 4 times longer than the first reduction reaction zone 220-1.

In embodiments including at least two reduction reaction zones, the zones can be separated from each other by a porous material, such as quartz or glass wool. The separation between reduction zones filled with porous material can have a length in a range of between 1% and 10%, preferably a length in a range of between 1% and 3%, of the length of the reactor. In one exemplary embodiment, the separation has a length of 0.5 cm or 1 cm, preferably 1 cm, for a reactor having a length of 470 mm.

As shown in FIG. 2B, the at least two reduction reaction zones can be three reduction reaction zones 220-1, 220-2, and 220-3. The relative lengths of the first and second reduction reaction zones can be as described above for the two zone reactor shown in FIG. 2D. Preferably, the third reduction reaction zone 220-3 is at least 1.1 times longer, or at least 1.2 times longer, or at least 1.5 times longer, or at least 2 times longer, or at least 2.5 times longer, or at least 3 times longer, or at least 4 times longer than the second reduction reaction zone 220-2. Preferably, the third reduction reaction zone 220-3 is up to 3 times longer, or up to 2 times longer, or up to 1.5 times longer than the second reduction reaction zone 220-2. In one exemplary embodiment, the first reduction reaction zone 220-1 has a length of 10 mm, the second reduction reaction zone 220-2 has a length of 40 mm, and the third reduction reaction zone 220-3 has a length of 50 mm. More than three reduction reaction zone scan be provided in some embodiments. The reactor zones graded in the way described herein provide a chemical gradient that increases the reaction speed and degree of reaction completion.

In certain embodiments, the elemental analysis system further includes a furnace 211 shown in FIG. 2A to heat the reactor 210, wherein the reduction reaction zone 220 and oxidation reaction zone 230 are each configured to be heated to a temperature in the range of between 150° C. and 1,200° C., such as a temperature in the range of between 750° C. and 1,200° C., or a temperature in the range of between 950° C. and 1,100° C.

Figure 3A:
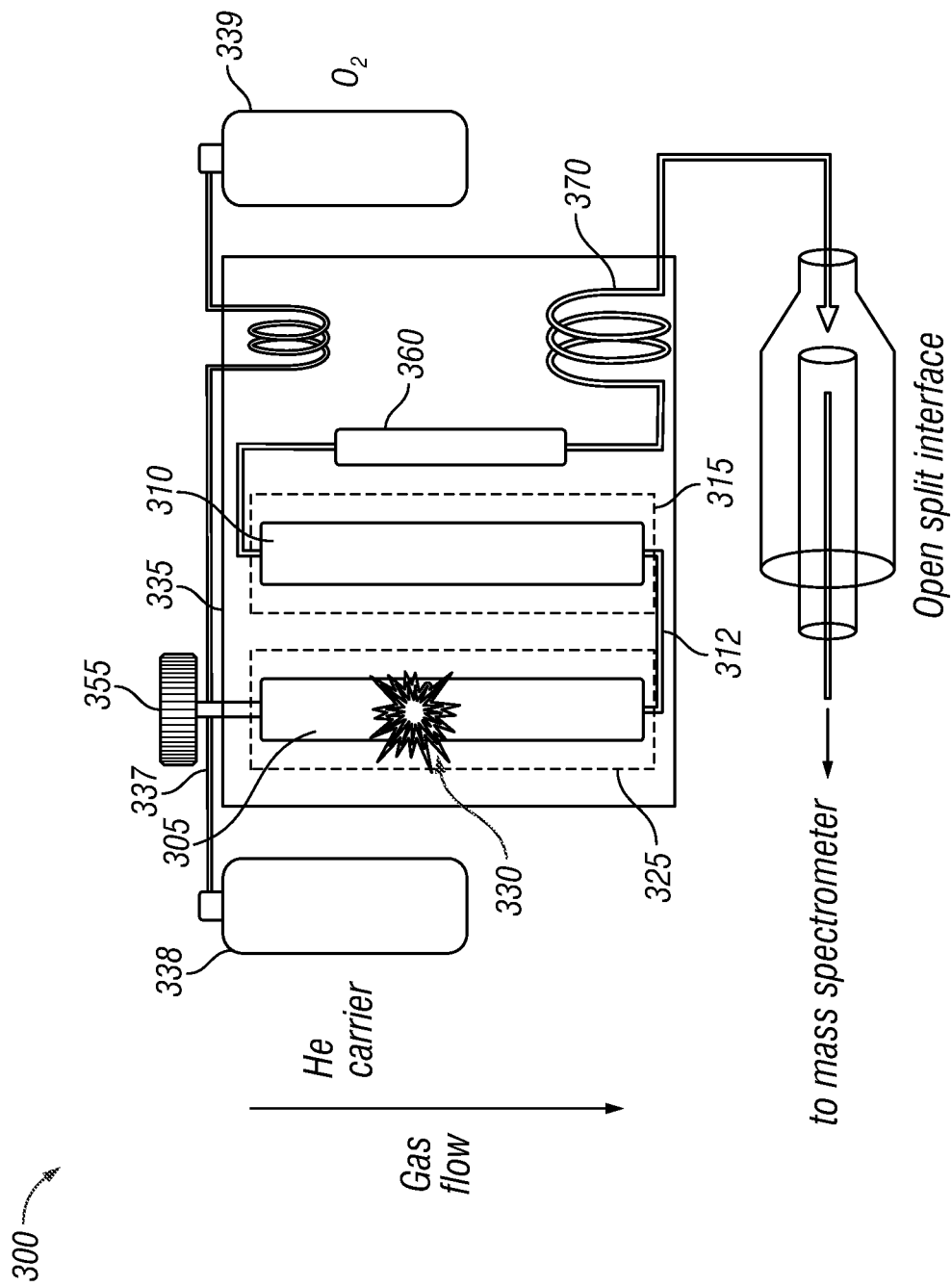
FIG. 3A is a schematic illustration of a two reactor elemental analysis system according to an exemplary embodiment of the invention.
Figure 3B:
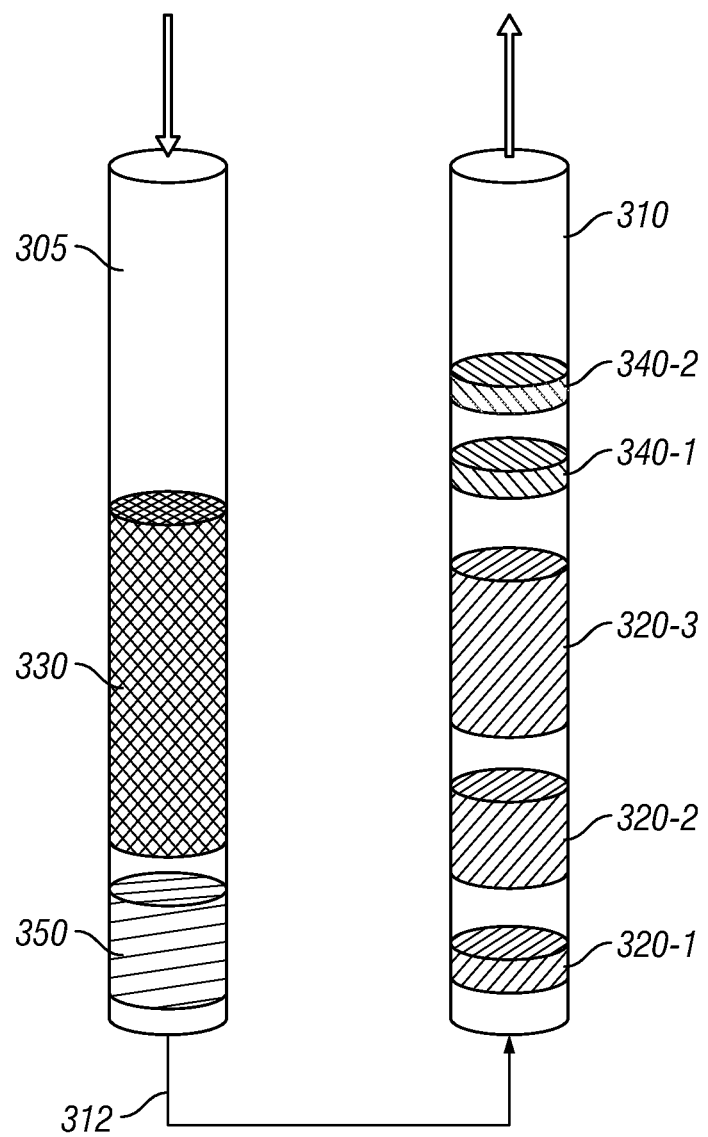
FIG. 3B is a schematic illustration of the two reactors of the elemental analysis system shown in FIG. 3A.

In the embodiment shown in FIGS. 3A and 3B, the elemental analysis system 300 can further include a second reactor 305 in fluid communication with a first reactor 310, the second reactor 305 being located upstream in a direction of gas flow through the first reactor 310, the second reactor 305 including an oxidation reaction zone 330. In this way, the first reactor 310 contains the at least one reduction reaction zone as described for FIGS. 2A-2D but without the oxidation reaction zone, which is instead located in the separate, second reactor 305. In these specific embodiments, the elemental analysis system 300 can further include a furnace 315 surrounding the first reactor 310 to heat the first reactor 310 to a temperature in the range of between 450° C. and 900° C., and a second furnace 325 surrounding the second reactor 305 to heat the second reactor 305 to a temperature in the range of between 150° C. and 1,200° C., such as a temperature in the range of between 750° C. and 1,200° C., or a temperature in the range of between 950° C. and 1,100° C. The second reactor 305 can further include an oxygen gas inlet 335 upstream of or into the oxidation reaction zone 330 for selectively permitting introduction of oxygen gas to the oxidation reaction zone 330. The second reactor 305 can further include a carrier gas inlet 337 for selectively permitting flow of carrier gas into the reactor 305, for example, the inlet 337 can be located at the upstream end of the reactor 305. Sources of He gas and $O_2$ gas in the form of gas bottles 338 and 339, respectively, are shown in FIG. 3A.

As shown in FIG. 3B, the oxidation reaction zone 330 can include an oxygen-donor material, such as at least one of chromium trioxide ($Cr_2O_3$), tungsten trioxide ($WO_3$), copper oxide, and a mixture of copper oxide and platinum-coated aluminum oxide. For elemental analysis limited to nitrogen and carbon, a Sulphur/halogen trap 350 is optionally located between 0 cm and 10 cm from the bottom of the second reactor 305. The Sulphur/halogen trap 350 can comprise i) silvered cobaltous oxide and/or silver vanadate, or ii) silver wool, packed in a length in a range of between 1% and 15% of the length of the second reactor 305, either in a single zone or multiple zones. The silver wool is preferably packed in a length in a range of between 1% and 8% of the length of the second reactor 305. The reactors 305 and 310 are fluidly connected via a stainless steel/sulfinert capillary 312, which may or may not be separately heated above 100° C. to minimize water condensation.

The arrangement and contents of the reduction reaction zone 320 and oxygen capture zone 340 in the first reactor 310 are similar to those described above for the reduction reaction zone 220 and oxygen capture zone 240, respectively. As shown in FIG. 3B, in an exemplary embodiment, the reduction reaction zones 320 are three reduction reaction zones 320-1, 320-2, and 320-3. Preferably, the third reduction reaction zone 320-3 is at least 1.1 times longer, or at least 1.2 times longer, or at least 1.5 times longer, or at least 2 times longer, or at least 2.5 times longer, or at least 3 times longer, or at least 4 times longer than the second reduction reaction zone 320-2. Preferably, the third reduction reaction zone 320-3 is up to 3 times longer, or up to 2 times longer, or up to 1.5 times longer than the second reduction reaction zone 320-2. In one exemplary embodiment, the first reduction reaction zone 320-1 has a length of 10 mm, the second reduction reaction zone 220-2 has a length of 40 mm, and the third reduction reaction zone 320-3 has a length of 50 mm, in a first reactor 310 having an overall length of 470 mm. As shown in FIG. 3B, the reactor 310 also optionally includes at least one oxygen capture zone 340 (two oxygen capture zones 340-1 and 340-2 shown in FIG. 3B), downstream (flow direction indicated by inlet and outlet arrows) of the reduction reaction zone 320, that can include metallic copper, metallic platinum, metallic nickel, or metallic cobalt, or any combination thereof. The total length of the oxygen capture zone 340 is in a range of between 1% and 15%, preferably in a range of between 1% and 8%, of the length of the reactor 310. In one aspect the oxygen capture zones 340-1 and 340-2 comprise metallic copper, in two zones each having a length of 20 mm, or two zones of successively increasing length in a direction of gas flow through the reactor, e.g., 20 mm preceded by 10 mm separated by a porous material, such as quartz or glass wool.

Turning back to FIG. 2A, after the gases are carried out of the reactor 210 (or the first reactor 310, not shown), they are swept through a water trap 260 (e.g., magnesium perchlorate) and/or a $CO_2$/acid gas trap (e.g., carbosorb, not shown). The reactor 210 is interfaced to a gas chromatography column 270 located downstream of the reactor 210 in a direction of gas flow. Alternatively, the reactor can be interfaced directly with a mass spectrometer 280 located downstream of the reactor 210 in a direction of gas flow through the reactor 210, optionally an isotope ratio mass spectrometer 280 of the magnetic sector multicollector type, as shown in FIG. 2A. The gas chromatography column 270 can be interfaced to a thermal conductivity detector (TCD) 275, or a flame ionization detector (FID) (not shown), an infrared (IR) detector (not shown), or a mass spectrometer, such as an isotope ratio mass spectrometer 280, as shown in FIG. 2A. The mass spectrometer is located downstream of the gas chromatography column 270 in a direction of gas flow, optionally an isotope ratio mass spectrometer including a magnetic sector mass analyzer. The gas inlet of the mass spectrometer can comprise an open split as shown in FIG. 2A, wherein the analyte gas (e.g., $CO_2$ and/or $N_2$ etc.) is diluted with further carrier gas prior to introduction into the mass spectrometer, as known in the art.

As shown in FIG. 3A, in embodiments including the second reactor 305, the first reactor 310 is interfaced to a gas chromatography column 370 located downstream of the first reactor 310 in a direction of gas flow and downstream of an optional water trap 360 (e.g., magnesium perchlorate) and/or a $CO_2$/acid gas trap (e.g., carbosorb, not shown). The gas chromatography column 370 can be interfaced to a thermal conductivity detector (TCD) (not shown), or a flame ionization detector (FID) (not shown), an infrared (IR) detector (not shown), or a mass spectrometer, such as an isotope ratio mass spectrometer (not shown). Alternatively, the first reactor can be interfaced directly with a mass spectrometer (not shown) located downstream of the first reactor 310 in a direction of gas flow through the first reactor 310. The mass spectrometer is, optionally, an isotope ratio mass spectrometer. An open split gas inlet interface into the mass spectrometer is shown in FIG. 3A.

As shown in FIG. 2A, the elemental analysis system 200 includes an autosampler 255, located upstream from the reactor 210, for introducing liquid 255-1 or solid 255-2 samples into the system 200. As shown in FIG. 3B, in embodiments including the second reactor 305, the elemental analysis system 300 includes an autosampler 355 located upstream from the second reactor 305 for introducing liquid or solid samples into the system 300. The samples are commonly sealed in tin capsules (alternatively, silver or aluminum capsules) and introduced to the combustion reactor 305 by the autosampler 355 in a flow of carrier gas. The capsule is broken down by heat and/or combustion in the reactor 305, releasing the sample, which is then broken down to form combustion products containing its elemental components.

Figure 4:
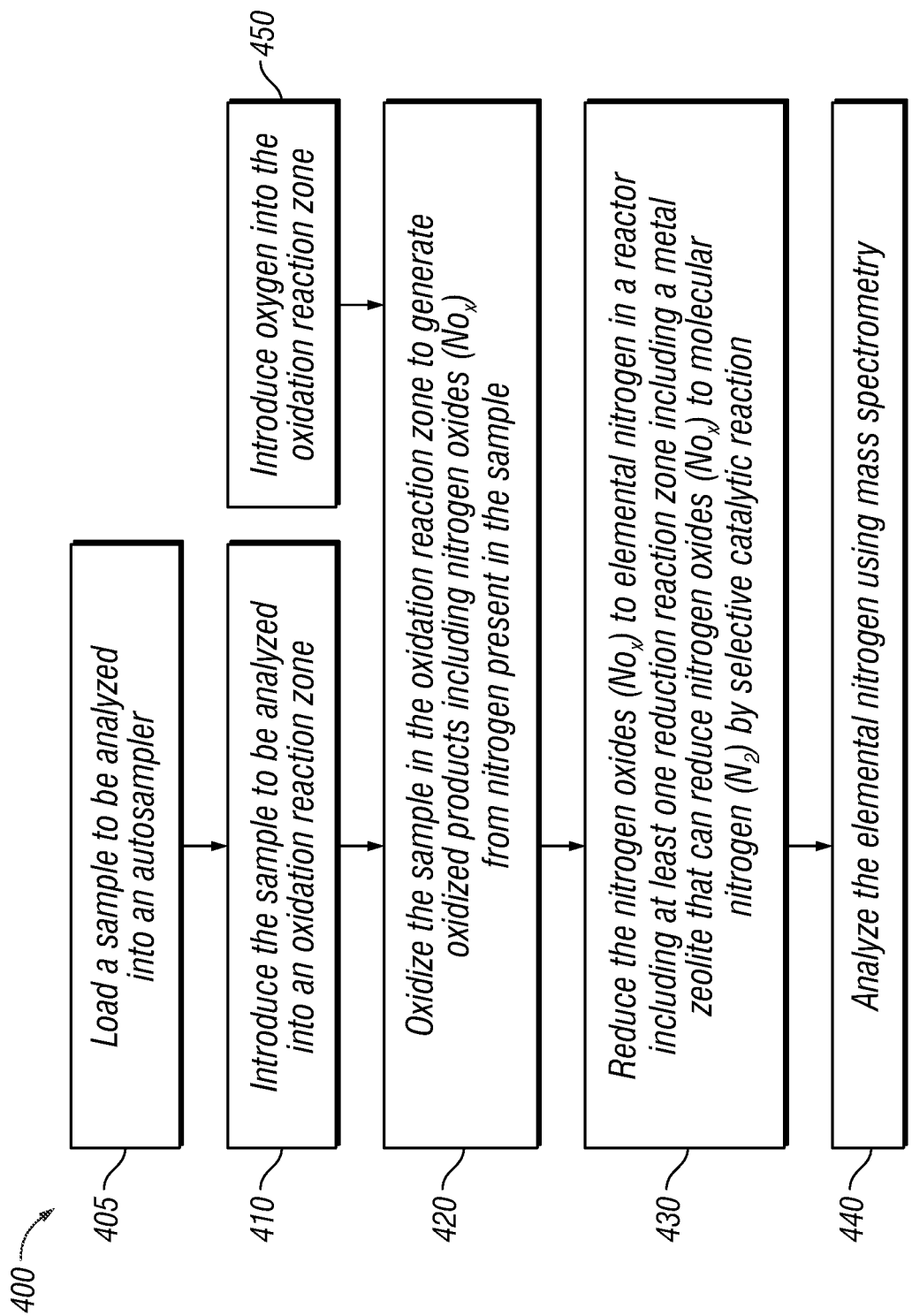
FIG. 4 is a flowchart of a method of elemental analysis of a sample according to an exemplary embodiment of the invention.

In another embodiment shown in FIG. 4, a method 400 of elemental analysis of a sample includes at step 410 introducing into an oxidation reaction zone a sample to be analyzed. The sample can be sealed in tin capsules (alternatively, silver or aluminum capsules), and, optionally, introduced by, at step 405, loading the samples into an autosampler prior to introduction to the reactor for processing. The method then comprises oxidizing at step 420 the sample in the oxidation reaction zone to generate oxidized products including nitrogen oxides ($NO_x$) from nitrogen present in the sample, reducing at step 430 the nitrogen oxides to elemental nitrogen in a reactor including at least one reduction reaction zone including a metal zeolite that can reduce nitrogen oxides ($NO_x$) to molecular nitrogen ($N_2$) by selective catalytic reaction, and analyzing at step 440 the elemental nitrogen using mass spectrometry. In some embodiments, the analyzing can include analyzing the molecular nitrogen ($N_2$) using isotope ratio mass spectrometry (IRMS) and determining therefrom isotope abundances or an isotope ratio $^{14}$N/$^{14}$N, $^{15}$N/$^{14}$N, and/or $^{15}$N/$^{15}$N, or a $\delta^{15}N$ value for the nitrogen from the sample material. In view of the improved reduction reaction efficiency of the zeolite compared to the metallic copper used for reduction in conventional EA reactor, the mass 30 peak can elute substantially simultaneously with mass 28 and mass 29 peaks in the IRMS analysis indicating it is due to $N_2$ rather than NO and therefore that the $NO_x$ to $N_2$ reduction reaction has been stoichiometric. The method can optionally further include at step 450 introducing oxygen upstream of and into the oxidation reaction zone.

EXEMPLIFICATION

Figure 5:
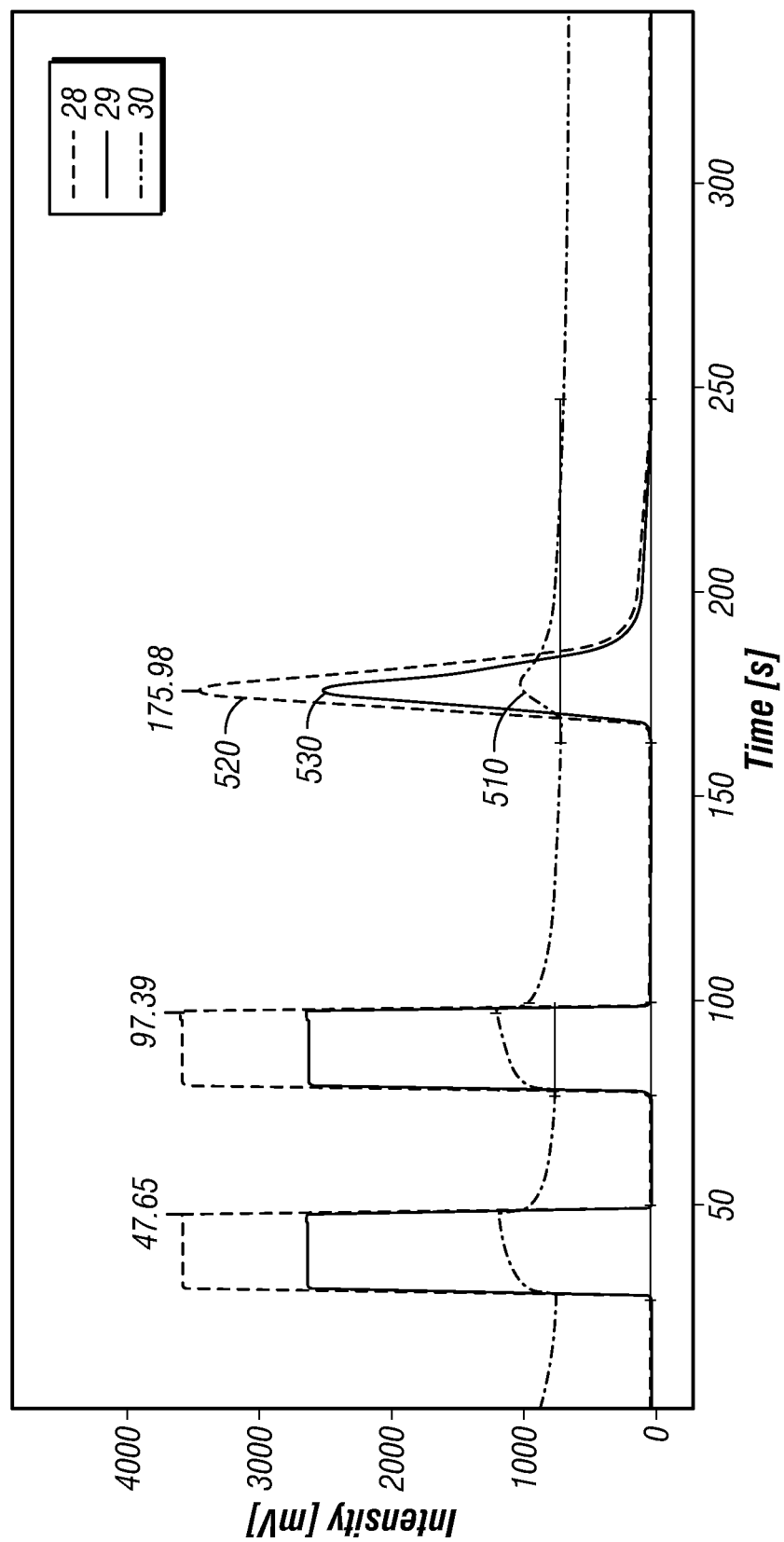
FIG. 5 is a chromatogram obtained from sample analysis from a single reactor elemental analysis system according to an exemplary embodiment of the invention throughout the entire reactor lifetime.
Figure 6:
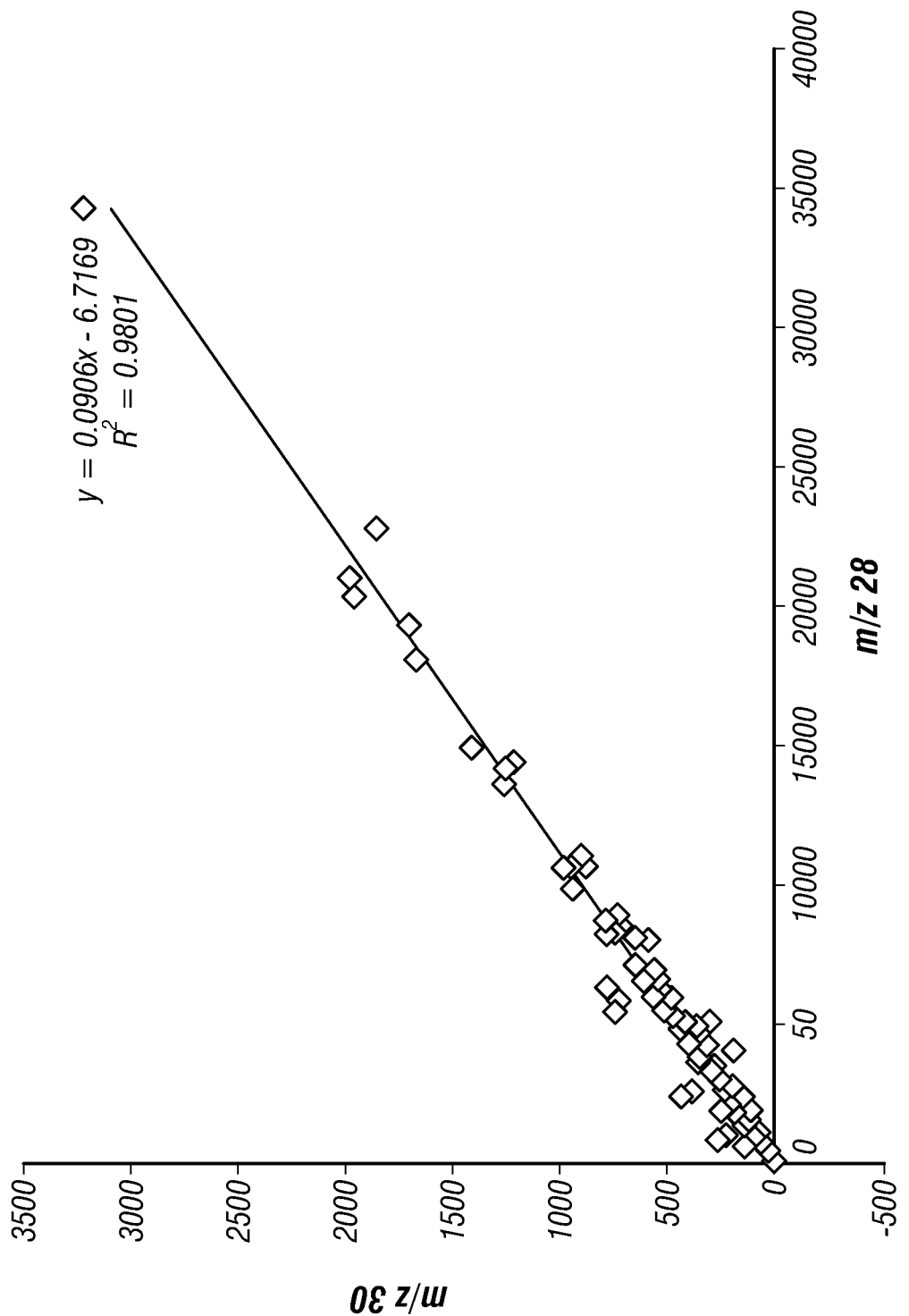
FIG. 6 is a graph of the mass 30 ion trace as a function of the mass 28 ion trace showing a linear correlation between intensity of the mass 30 and mass 28 ion traces from 166 contiguous samples processed within one reactor according to an exemplary embodiment of the invention.

As shown in FIG. 5, using the reactor shown in FIGS. 2A and 2B, the behaviour of the mass 30 ion trace 510 has been completely altered. Now, from the analysis of the first sample, the mass 30 ion trace 510 is linearly correlated to that of the mass 28 and mass 29 ion traces 520 and 530, respectively, and chromatographically coherent. Consequently, the accuracy and precision of $\delta^{15}N$ values has significantly improved as determined on international isotopic reference materials. In addition, as shown in FIG. 6, a linear correlation was observed between the intensity of the mass 30 and mass 28 ion traces from 166 contiguous samples processed within one reactor as shown in FIGS. 2A and 2B.

Figure 7:
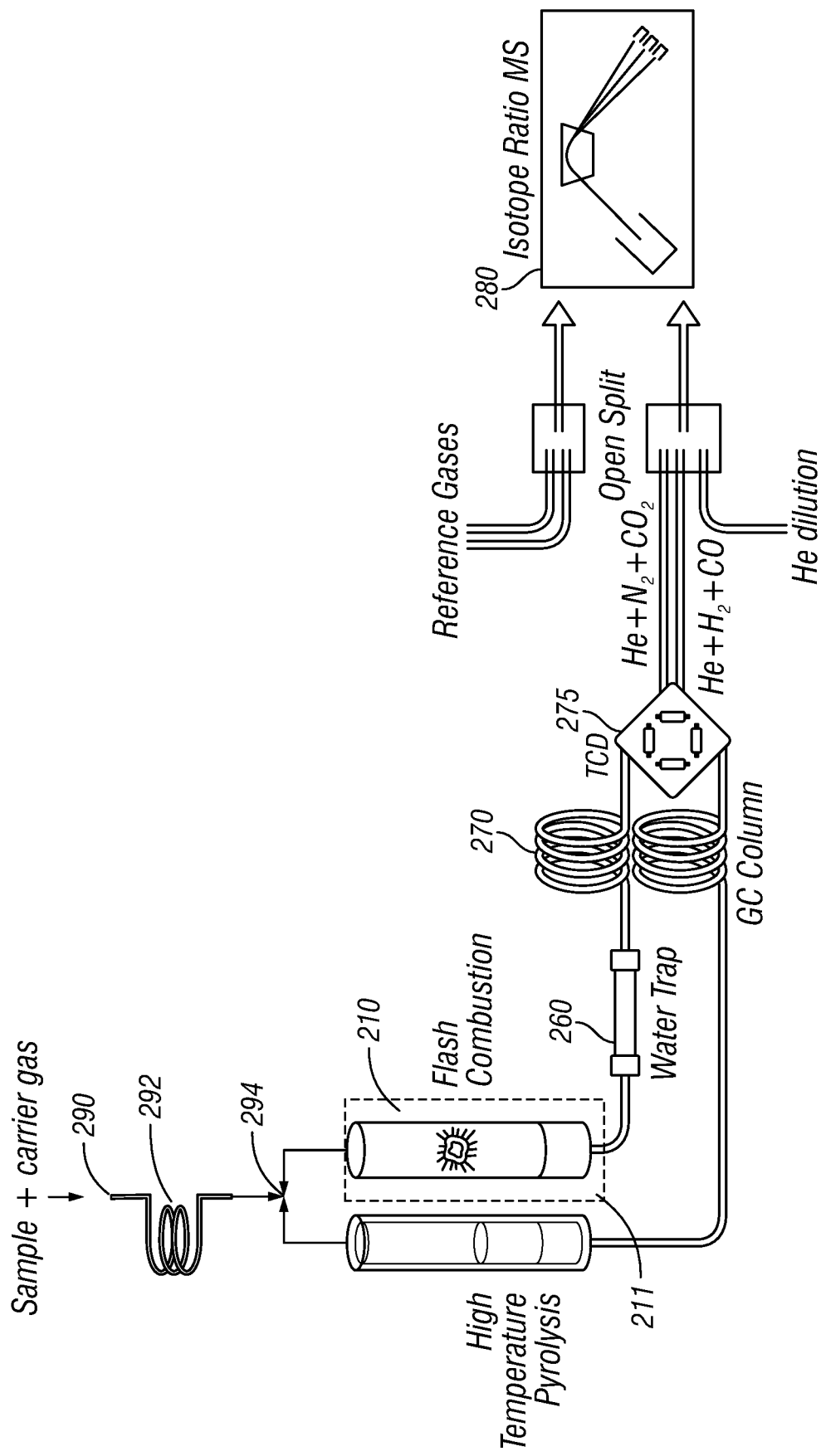
FIG. 7 is a schematic illustration of an elemental analysis system according to an exemplary embodiment of the invention having a GC column interfaced to the inlet of a reactor.

The reactor of the present invention can be used in a GC-MS, or GC-IRMS instrument (for example based on a Thermo Scientific Isotope Ratio Mass Spectrometer). In other embodiments, the reactor of the present invention can be employed in an LC-IRMS system, for example of the type described in US 2011-212536 A, the contents of which is incorporated herein in its entirety. In such systems, a chromatography column (gas or liquid chromatography column) is provided upstream of the reactor for separating compounds of a sample upstream of the reactor. The elemental analysis and/or isotope ratio analysis can then be performed on the separated compounds in sequence, or on selected compounds eluting from the column. In GC/IRMS systems, the sample is typically injected into a gas chromatography (GC) inlet where it is carried into a chromatographic column by a carrier gas (e.g. helium). The sample and carrier gas flows through the column and the different compounds in the sample become separated and elute from the column at different times (retention times). The separate compounds eluting from the chromatographic column in sequence then pass through the reactor (i.e. comprising the oxidation reactor to combust the compounds, followed by the reduction reactor to reduce nitrogen oxides to nitrogen). Optionally, a switching valve can be placed between the column and the reactor, which can be switched at the appropriate time, so that only compounds of interest can be selected and directed into the reactor, with compounds not of interest being directed to a waste line or similar at other times. The same options for chemical traps as described hereinabove may be used in the system. The oxidized/reduced gases are then introduced, optionally via a further gas chromatography column to separate the gases, into the ion source of the mass spectrometer, optionally via an open split interface, for elemental analysis and/or isotope ratio analysis. Such a system for GC is shown in FIG. 7, which is analogous to the system of FIG. 2 but having a GC column 292 interfaced via valve 294 to the inlet of the reactor 210. A sample and carrier gas is introduced into the column 292 via GC inlet 290. A high temperature pyrolysis reactor, for alternative use to the reactor of the invention, is included optionally for H or O analysis and can be selected by the valve 294 if required. Accordingly, in some embodiments, the reactor is interfaced to a chromatography column, especially a gas chromatography column, located upstream of the reactor, preferably wherein an isotope ratio mass spectrometer is located downstream of the reactor. A further chromatography column 270, especially a gas chromatography column, can be located downstream of the reactor, i.e. intermediate between the reactor and the mass spectrometer.

Figure 8:
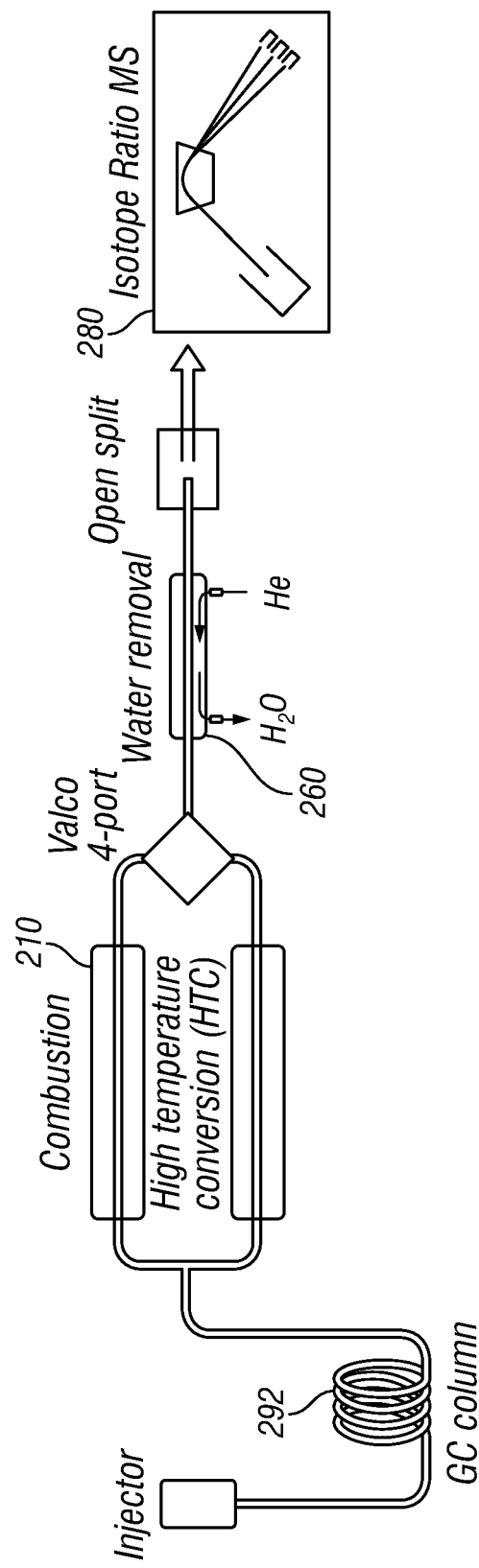
FIG. 8 is a schematic illustration of an elemental analysis system according to another exemplary embodiment of the invention having a GC column interfaced to the inlet of a reactor.

In other embodiments of a GC/IRMS system according to the invention, a further chromatography column downstream of the reactor may be omitted. Such a system is shown schematically in FIG. 8, wherein components corresponding to components shown in earlier figures are given like reference numerals.

Figure 9:
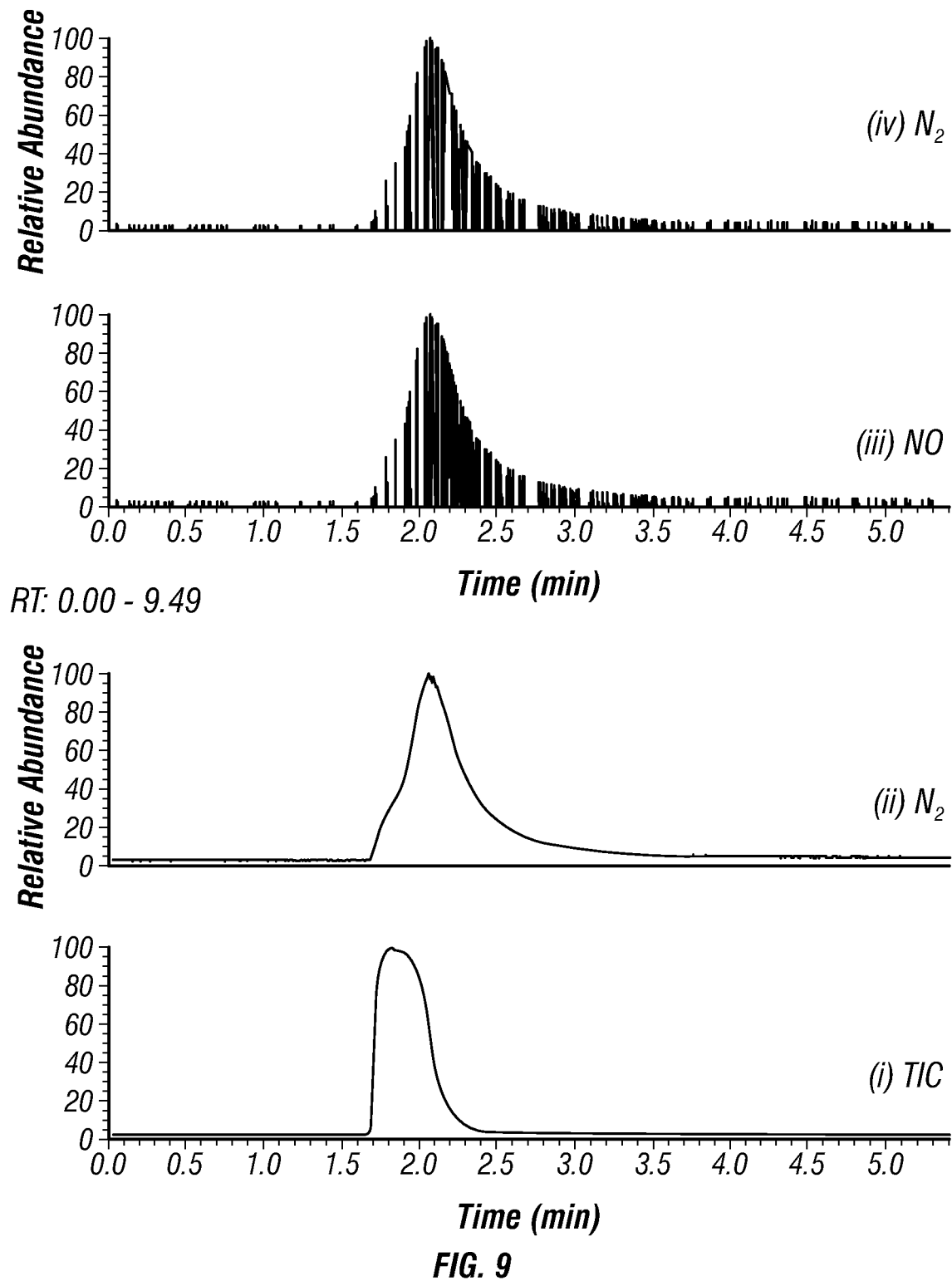
FIG. 9 is a set of chromatograms obtained from sample analysis from a GC-MS elemental analysis system according to a single reactor prior art embodiment.
Figure 10:
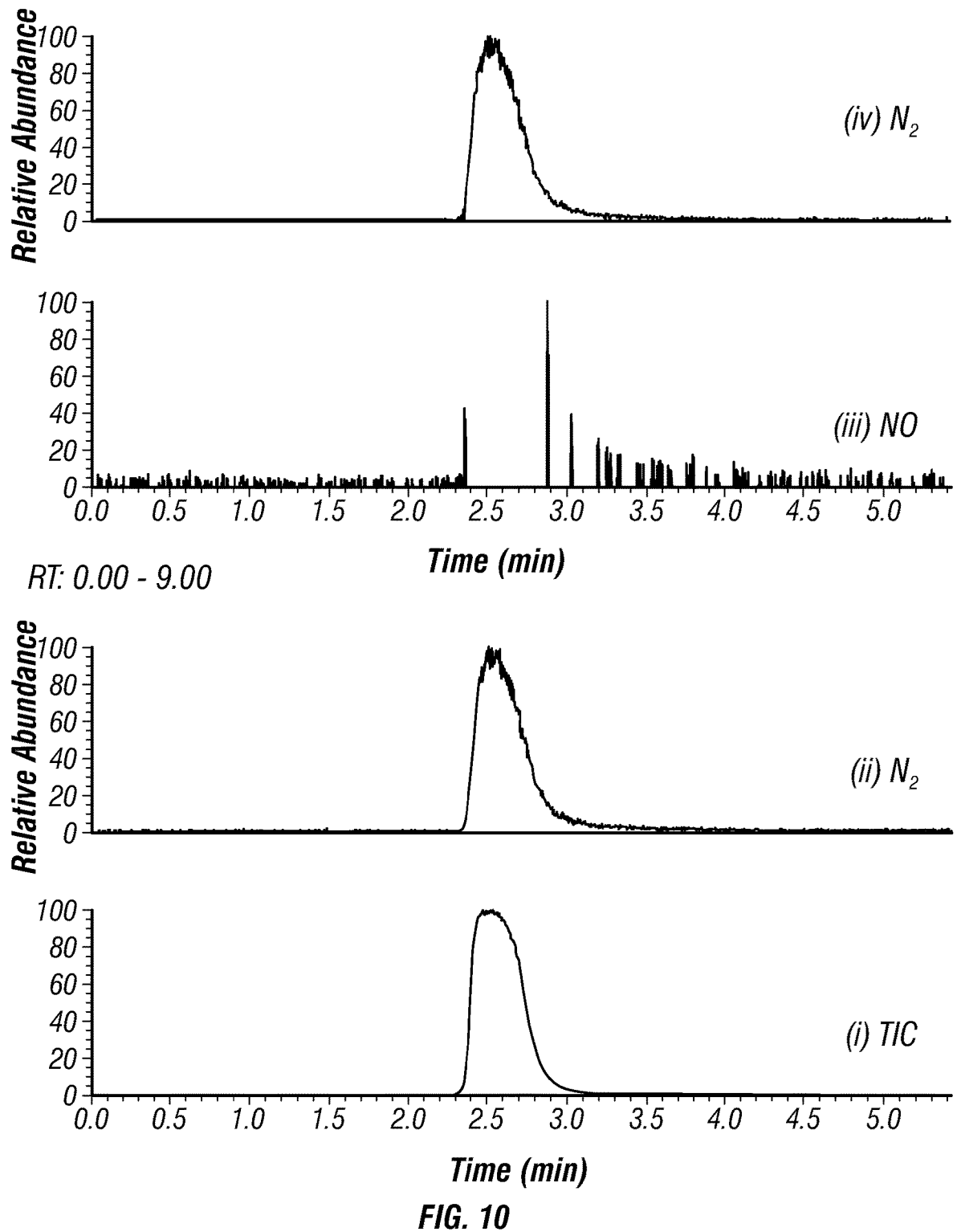
FIG. 10 is a set of chromatograms obtained from sample analysis from a GC-MS elemental analysis system according to a single reactor exemplary embodiment of the invention.

The advantageous effects of the present invention are further illustrated by the chromatograms shown in FIGS. 9 and 10. FIG. 9 shows a set of chromatograms obtained from sample analysis by GC-MS from an elemental analysis system according to a single reactor prior art embodiment, wherein the reduction reactor comprises metallic copper. In chromatogram (i) of FIG. 9, the total ion current (TIC) trace from the mass spectrometer measurement is shown and chromatogram (iv) shows the evolution of the $N_2$ species (masses 28, 29, 30). However, the size of the mass resolved NO peak in chromatogram (iii) is significant in relation to the $N_2$, i.e. the $N_2$ and NO are both present in relatively similar amounts, showing an incomplete $NO_x$ conversion, which affects the shape of the mass 30 $^{15}N_2$ chromatogram in chromatogram (ii).

In contrast, FIG. 10 shows a set of chromatograms obtained from sample analysis by GC-MS from an elemental analysis system according to a single reactor exemplary embodiment of the invention. As shown in the chromatogram (iii), the NO trace is virtually absent (below the limit of detection), because of the quantitative conversion of NO to $N_2$ on the zeolite in the reduction reactor. Accordingly, the shape of the $N_2$ traces (ii) and (iv) are improved and align well with the TIC trace (i).

While the present invention has been illustrated by a description of exemplary embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An elemental analysis system comprising: a first reactor including at least two reduction reaction zones, each reduction reaction zone including a metal zeolite that reduces nitrogen oxides ($NO_x$) to molecular nitrogen ($N_2$) by selective catalytic reaction, wherein an oxidation reaction zone is provided either (i) in the first reactor such that the oxidation reaction zone is located before the reduction reaction zones in a direction of gas flow through the first reactor, or (ii) in a second reactor in fluid communication with the first, the second reactor being located upstream of the first reactor in the direction of gas flow through the first reactor; and a mass spectrometer positioned downstream of the first reactor; wherein the at least two reduction reaction zones are separated from each other by a porous material.

2. The system of claim 1, wherein the metal zeolite is a ZSM-5 type material.

3. The system of claim 1, wherein the metal zeolite comprises a +2 oxidation state metal.

4. The system of claim 3, wherein the +2 oxidation state metal is at least one of copper, platinum, nickel, and cobalt.

5. The system of claim 1, wherein the metal content of the metal zeolite is in a range of between 2.1 wt % and 5.0 wt %.

6. The system of claim 1, wherein the metal zeolite has a grain size in a range of between 0.3 mm and 2.9 mm.

7. The system of claim 1, wherein the metal zeolite comprises carbon in an amount that is at least 70 ppm and less than 200 ppm.

8. The system of claim 1, wherein the at least two reduction reaction zones are of substantially the same length or of successively increasing lengths in the direction of gas flow through the first reactor, the lengths being in total in a range of between 1% and 30% of a length of the first reactor.

9. The system of claim 8, wherein the at least two reduction reaction zones are separated from each other by a length in a range of between 1% and 3% of a length of the first reactor.

10. The system of claim 1, wherein the porous material comprises quartz or glass wool.

11. The system of claim 1, wherein the first reactor further includes an oxygen gas inlet upstream of or into the oxidation reaction zone.

12. The system of claim 1, wherein the oxidation reaction zone includes an oxygen-donor material.

13. The system of claim 12, wherein the oxygen-donor material comprises at least one of chromium trioxide ($Cr_2O_3$), tungsten trioxide ($WO_3$), copper oxide, and a mixture of copper oxide and platinum-coated aluminum oxide.

14. The system of claim 1, further including a furnace to heat the first reactor, wherein each of the reduction reaction zones and the oxidation reaction zone are each configured to be heated to a temperature in the range of between 150° C. and 1,200° C.

15. The system of claim 14, wherein each of the reduction reaction zones are configured to be heated to a lower temperature than the oxidation reaction zone.

16. The system of claim 1, further including an oxygen capture zone, downstream of each of the reduction reaction zones, that comprises metallic copper, metallic platinum, metallic nickel, or metallic cobalt, or any combination thereof.

17. The system of claim 1, wherein the oxidation reaction zone is located in the second reactor.

18. The system of claim 17, further including a furnace to heat the first reactor to a temperature in the range of between 150° C. and 1,200° C., and a second furnace to heat the second reactor to a temperature in the range of between 150° C. and 1,200° C.

19. The system of claim 17, wherein the second reactor further includes an oxygen gas inlet upstream of or into the oxidation reaction zone.

20. The system of claim 17, wherein the oxidation reaction zone includes an oxygen-donor material.

21. The system of claim 20, wherein the oxygen-donor material comprises at least one of chromium trioxide ($Cr_2O_3$), tungsten trioxide ($WO_3$), copper oxide, and a mixture of copper oxide and platinum-coated aluminum oxide.

22. The system of claim 17, wherein the first reactor is interfaced to a gas chromatography column located downstream of the first reactor in a direction of gas flow.

23. The system of claim 22, wherein the gas chromatography column is interfaced to the mass spectrometer.

24. The system of claim 17, further including an autosampler located upstream from the second reactor for introducing liquid or solid samples into the system.

25. The system of claim 1, wherein the first reactor is interfaced to a gas chromatography column located downstream of the first reactor in a direction of gas flow.

26. The system of claim 25, wherein the gas chromatography column is interfaced to the mass spectrometer.

27. The system of claim 1, wherein the first reactor is interfaced to a gas chromatography column located upstream of the first reactor in a direction of gas flow.

28. The system of claim 1, further including an autosampler located upstream from the first reactor for introducing liquid or solid samples into the system.

29. A method of elemental analysis of a sample, the method comprising:
a. introducing into an oxidation reaction zone a sample to be analyzed;

b. oxidizing the sample in the oxidation reaction zone to generate oxidized products including nitrogen oxides ($NO_x$) from nitrogen present in the sample;

c. reducing the nitrogen oxides to elemental nitrogen in a reactor including at least two reduction reaction zones, each of the reduction reaction zones including a metal zeolite that can reduce nitrogen oxides ($NO_x$) to molecular nitrogen ($N_2$) by selective catalytic reaction, the at least two reduction reaction zones being separated from each other by a porous material; and d. analyzing the elemental nitrogen using mass spectrometry.

30. The method of claim 29, wherein the analyzing comprises analyzing the molecular nitrogen ($N_2$) using isotope ratio mass spectrometry (IRMS) and determining therefrom an isotope ratio $^{14}$N/$^{14}$N, $^{15}$N/$^{14}$N, and $^{15}$N/$^{15}$N, and subsequently calculating a $\delta^{15}N$ value for the nitrogen produced from the sample material.

31. The method of claim 30, wherein in the IRMS analysis the mass 30 peak elutes simultaneously with mass 28 and mass 29 peaks.

32. The method of claim 29, further including introducing oxygen upstream of or into the oxidation reaction zone.

33. The method of claim 29, wherein the sample to be analyzed is introduced into the oxidation reaction zone using a liquid or solid autosampler.

* * * * *